(12) United States Patent
Burkinshaw et al.

(10) Patent No.: US 8,206,448 B2
(45) Date of Patent: Jun. 26, 2012

(54) INJECTION OF FIBRIN SEALANT USING RECONSTITUTED COMPONENTS IN SPINAL APPLICATIONS

(75) Inventors: Brian D. Burkinshaw, Pflugerville, TX (US); Steven I. Whitlock, Austin, TX (US); Kevin Pauza, Tyler, TX (US); Mark I. Richards, Leander, TX (US); James B. Rogan, Austin, TX (US)

(73) Assignee: Spinal Restoration, Inc., Austin, TX (US)

( * ) Notice: Subject to any disclaimer, the term of this patent is extended or adjusted under 35 U.S.C. 154(b) by 1212 days.

(21) Appl. No.: 11/205,784

(22) Filed: Aug. 17, 2005

(65) Prior Publication Data

US 2006/0095075 A1 May 4, 2006

Related U.S. Application Data

(60) Provisional application No. 60/623,600, filed on Oct. 29, 2004.

(51) Int. Cl.
*A61F 2/44* (2006.01)
(52) U.S. Cl. ..................................... 623/17.16
(58) Field of Classification Search .......... 604/191; 606/213–215; 623/17.16
See application file for complete search history.

(56) References Cited

U.S. PATENT DOCUMENTS

| | | | |
|---|---|---|---|
| 2,533,004 A | 12/1950 | Ferry et al. | 260/112 |
| 3,089,815 A | 5/1963 | Lieb et al. | 167/58 |
| 4,240,946 A * | 12/1980 | Hemersam | 524/71 |
| 4,249,464 A * | 2/1981 | Hansen | 99/450 |
| 4,359,049 A | 11/1982 | Redl et al. | 128/218 PA |
| 4,393,041 A | 7/1983 | Brown et al. | 424/19 |
| 4,427,650 A | 1/1984 | Stroetmann | 424/46 |
| 4,442,655 A * | 4/1984 | Stroetmann | 53/428 |
| 4,619,913 A | 10/1986 | Luck et al. | 514/131 |
| 4,631,055 A * | 12/1986 | Redl et al. | 604/82 |
| 4,714,457 A * | 12/1987 | Alterbaum | 494/37 |
| RE33,375 E | 10/1990 | Luck et al. | 514/2 |
| 5,124,155 A | 6/1992 | Reich | 424/428 |
| 5,219,328 A * | 6/1993 | Morse et al. | 604/500 |

(Continued)

FOREIGN PATENT DOCUMENTS

DE 3037270 5/1982

(Continued)

OTHER PUBLICATIONS

"Effects of Cellular Composition on Clotting Time." http://ieeexplore.ieee.org/stamp/stamp.jsp?arnumber=01629811.*

(Continued)

*Primary Examiner* — Christopher D Koharski
*Assistant Examiner* — Diva K Chander
(74) *Attorney, Agent, or Firm* — O'Keefe, Egan, Peterman & Enders, LLP

(57) ABSTRACT

A method of treating a disc that is leaking nucleus pulposus through at least one defect in the annulus fibrosus. The method includes injecting a fibrin sealant into the disc to reduce at least a portion of the at least one defect, wherein the fibrin sealant injected into the disc comprises fibrinogen and an activating compound, wherein at least a portion of the fibrin forms after injection, wherein the fibrinogen, the activating compound or both has been reconstituted with a solution containing at least one additive, with the proviso that a corticosteroid is absent from the fibrin sealant injected into the disc.

26 Claims, 4 Drawing Sheets

U.S. PATENT DOCUMENTS

| | | | | |
|---|---|---|---|---|
| 5,264,446 | A | | 11/1993 | Hegasy et al. ............... 514/356 |
| 5,290,552 | A | * | 3/1994 | Sierra et al. ............... 424/94.64 |
| 5,643,192 | A | | 7/1997 | Hirsh et al. ...................... 604/4 |
| 5,651,982 | A | | 7/1997 | Marx ............................ 424/450 |
| 5,702,715 | A | | 12/1997 | Nikolaychik et al. ......... 424/402 |
| 5,925,738 | A | | 7/1999 | Miekka et al. ............... 530/380 |
| 5,962,420 | A | | 10/1999 | Edwardson et al. ............ 514/21 |
| 5,980,504 | A | | 11/1999 | Sharkey et al. ............... 604/510 |
| 5,980,866 | A | | 11/1999 | Uchida et al. .................. 424/45 |
| 6,007,570 | A | * | 12/1999 | Sharkey et al. ................. 607/96 |
| 6,007,811 | A | | 12/1999 | Sawyer et al. ............. 424/94.64 |
| 6,054,122 | A | | 4/2000 | MacPhee et al. ............ 424/94.4 |
| 6,073,051 | A | | 6/2000 | Sharkey et al. ................. 607/99 |
| 6,117,425 | A | | 9/2000 | MacPhee et al. .......... 424/94.64 |
| 6,122,549 | A | | 9/2000 | Sharkey et al. ................. 607/99 |
| 6,124,273 | A | | 9/2000 | Drohan et al. .................. 514/55 |
| 6,126,682 | A | | 10/2000 | Sharkey et al. ................. 607/96 |
| 6,183,518 | B1 | | 2/2001 | Ross et al. ................. 623/17.16 |
| 6,197,325 | B1 | | 3/2001 | MacPhee et al. .............. 424/426 |
| 6,224,630 | B1 | * | 5/2001 | Bao et al. .................. 623/17.16 |
| 6,231,716 | B1 | * | 5/2001 | White et al. ............. 156/345.54 |
| 6,258,086 | B1 | | 7/2001 | Ashley et al. .................. 606/41 |
| 6,261,311 | B1 | | 7/2001 | Sharkey et al. ................. 607/96 |
| 6,320,029 | B1 | | 11/2001 | Miekka et al. ............... 530/380 |
| 6,428,576 | B1 | | 8/2002 | Haldimann ................ 623/17.16 |
| 6,468,527 | B2 | | 10/2002 | Austin et al. .............. 424/94.64 |
| 6,517,568 | B1 | | 2/2003 | Sharkey et al. ................. 607/96 |
| 6,547,810 | B1 | | 4/2003 | Sharkey et al. ................. 607/96 |
| 6,559,119 | B1 | | 5/2003 | Burgess et al. .................. 514/2 |
| 6,638,276 | B2 | | 10/2003 | Sharkey et al. ................. 606/41 |
| 6,648,852 | B2 | * | 11/2003 | Wirt et al. ....................... 604/86 |
| RE38,431 | E | | 2/2004 | Miekka et al. ............... 530/380 |
| 6,723,095 | B2 | * | 4/2004 | Hammerslag ................... 606/60 |
| 6,726,685 | B2 | | 4/2004 | To et al. .......................... 606/50 |
| 6,733,496 | B2 | | 5/2004 | Sharkey et al. ................. 606/41 |
| 6,749,605 | B2 | | 6/2004 | Ashley et al. .................. 606/41 |
| 6,762,336 | B1 | | 7/2004 | MacPhee et al. ............... 602/48 |
| 6,767,347 | B2 | | 7/2004 | Sharkey et al. ................. 606/41 |
| 6,921,532 | B1 | | 7/2005 | Austin et al. .............. 424/94.64 |
| 7,004,945 | B2 | | 2/2006 | Boyd et al. ...................... 606/41 |
| 7,196,054 | B1 | * | 3/2007 | Drohan et al. ................. 514/9.4 |
| 7,449,019 | B2 | * | 11/2008 | Uchida et al. .................. 606/27 |
| 2002/0198599 | A1 | * | 12/2002 | Haldimann ................ 623/17.16 |
| 2003/0104032 | A1 | * | 6/2003 | Sawhney et al. .............. 424/426 |
| 2003/0181964 | A1 | | 9/2003 | Sharkey et al. ................. 607/96 |
| 2003/0187387 | A1 | * | 10/2003 | Wirt et al. ....................... 604/82 |
| 2004/0111136 | A1 | | 6/2004 | Sharkey et al. ................. 607/99 |
| 2004/0193151 | A1 | | 9/2004 | To et al. .......................... 606/41 |
| 2005/0118156 | A1 | * | 6/2005 | Woolverton .................. 424/94.6 |
| 2007/0191781 | A1 | * | 8/2007 | Richards et al. .............. 604/191 |

FOREIGN PATENT DOCUMENTS

| | | |
|---|---|---|
| EP | 0 068 149 | 5/1982 |
| WO | WO81/00516 | 3/1981 |
| WO | WO92/22312 | 12/1992 |
| WO | WO94/20133 | 9/1994 |
| WO | WO96/17633 | 6/1996 |
| WO | WO97/42986 | 11/1997 |
| WO | WO01/97872 | 12/2001 |

OTHER PUBLICATIONS

US 6,645,204, 11/2003, Sharkey et al. (withdrawn).
Abstract: T. Yagita, "Agent for Controlling Formation of Cheloid at Excision Site for Inflammation Bowel Disease" Feb. 10, 1997; Database WPI, Section Ch, Week 199716, Derwent Publications Ltd., London, GB XP002182938.
Abstract: Sumitomo Cement Co., "Sustained Release Agent for Treatment of Osteomyelitis" Jan. 8, 1993; Database WPI, Section Ch, Week 199306, Derwent Publications Ltd., London, GB XP002182939.
G.Y. Bong et al., "Development of Local Antibiotic Delivery System Using Fibrin Glue" Mar. 1, 1996; Journal of Controlled Release, Elsevier Science Publishers, vol. 29, No. 1, pp. 65-70.
J. Rousou et al., "Randomized Clinical Trial of Fibrin Sealant in Cardiac Surgery Patients Undergoing Resternotomy" Feb. 1989; Journal of Thoracic and Cardiovascular Surgery; vol. 97, No. 2, pp. 194-203.
P. Knoringer, "Fibrin Sealing in Spinal Neurosurgery" 1986.
P.M. McCarthy et al., "Fibrin Sealant: The Cleveland Clinic Experience" 1991.
M. Dahan et al., "The Importance of Biological Glue for the Prevention of Air Leakage in Pulmonary Surgery" 1991; Materials and Methods, pp. 113-116.
H. W. Waclawiczek, "Fibrin Sealing in Liver and Spleen Surgery" 1994.
C. Shaffey et al., "Neurosurgical Applications of Fibrin Glue: Augmentation of Dural Closure in 134 Patients" 1990; Neurosurgery, vol. 26, No. 2, pp. 207-210.
M. Acqui et al., "Our Experience With Human Fibrin Glue in Neurological Procedures" Date unknown.
A. Hjortrup, M.D. et al., "Fibrin Adhesive in Perineal Fistulas" Sep. 1991; from the Dept. of Surgical Gastroenterology F, Bispebjerg Hospital and Dept. of Surgical Gastroenterology C, Rigsbospitalet, University of Copenhagen, Copenhagen, Denmark, vol. 34, No. 9.
T. M. Kieser et al., "Reduced Postoperative Bleeding Following Use of Tisseel Fibrin Sealant in 300 Patients undergoing Open-Heart Surgery" date unknown.
W. D. Sponitz, M.D. et al., "Clinical Uses of Fibrin Sealant" 1999; Transfusion Therapy: Clinical Principles and Practice, Bethesda, MD: AABB Press.
N. Tajima et al., "Bone Grafts Using Fibrin Glue for Posterolateral Spinal Fusion and Total Hip Replacement with Central Migration" date unknown.
G. E. Lutz et al., "Flouroscopic Transforaminal Lumbar Epidural Steroids: An Outcome Study" Nov. 1998; Arch Phys Med Rehabil, vol. 79, pp. 18-21.
P. Goupille et al., "The Role of Inflammation in Disk Herniation-Associated Radiculopathy" Aug. 28, 1998; Semin Arthritis Rheum, (1):60-71.
J. D. Kang et al., "Herniated Lumbar Intervertebral Discs Spontaneously Produce Matrix Metalloproteinases, Nitric Oxide, Interleukin-6, and Prostaglandin E2" Feb. 1, 1996; Spine, 21(3): 271-7.
J. S. Saal et al., "High Levels of Inflammatory Phospholipase A2 Activity in Lumbar Disc Herniations" Jul. 1990; Spine, 15(7): 674-8.
O. P. Nygaard et al., "The Inflammatory Properties of Contained and Noncontained Lumbar Disc Herniation" Nov. 1, 1997; Spine, 22(21): 2484-8.
H. Takahashi et al., "Inflammatory Cytokines in the Herniated Disc of the Lumbar Spine" Jan. 15, 1996; Spine, 21(2):218-24.
Product Information, "Celestone Soluspan", brand of betamethasone sodium phosphate and betamethasone acetate Injectable Suspension, USP 6 mg. per mL, Schering Corporation, Kenilworth, N.J. 07033 USA, Rev. Mar. 1996.
Product Information, "Fibrin Sealant Hemaseel APR Kit, Two Component Fibrin Sealant, Vapor Heated, Kit" Manufactured for and Distributed by Haemacure Corp., 2 N. Tamiami Trail, Suite 802, Sarasota, FL 34236, Issued May 1998.

* cited by examiner

INJECTION OF FIBRIN SEALANT USING RECONSTITUTED COMPONENTS IN SPINAL APPLICATIONS

This application claims priority to U.S. provisional application No. 60/623,600, filed Oct. 29, 2004, incorporated herein by reference.

BACKGROUND OF THE INVENTION

The present invention relates generally to the use of fibrin sealant whereby the sealant is delivered such as by injection to the spinal area, and the fibrinogen and/or thrombin is reconstituted using a solution containing an additive.

Fibrin sealants, and glues, are well known and are used extensively in various clinical settings. Such sealants are indicated as adjuncts to hemostasis in surgeries when control of bleeding by conventional surgical techniques, including suture, ligature, and cautery is ineffective or impractical. In these cases, the sealant was applied topically.

Recently, fibrin sealant that included a corticosteroid was used to treat disc problems such as fissures in the annulus fibrosus. In this regard, U.S. Pat. No. 6,468,527 discloses that the composition was injected into a disc (an intra-discal injection) to treat disc problems.

SUMMARY OF THE INVENTION

In the practice of the present invention, fibrin sealant is injected into the spinal area of a human being. The sealant comprises fibrinogen and an activating compound such as thrombin, which form fibrin when mixed. It has been found that this composition provides surprisingly superior results relative to fibrin sealant compositions containing a corticosteroid. Calcium ions, such as supplied from calcium chloride, may be included in the fibrin sealant. The fibrinogen and/or thrombin may be derived from a freeze-dried component that is reconstituted with a solution containing one or more additives, such as various biological and non-biological agents. The use of the one or more additives provides superior results. However, corticosteroids are excluded from the fibrin sealant.

In one broad respect, this invention is a method of treating a disc that is leaking nucleus pulposus through at least one defect in the annulus fibrosus, comprising: injecting a fibrin sealant into the disc to reduce at least a portion of the at least one defect, wherein the fibrin sealant injected into the disc comprises fibrinogen and an activating compound such as thrombin, wherein at least a portion of the fibrin forms after injection, wherein the fibrinogen, the activating compound or both has been reconstituted with a solution containing at least one additive, with the proviso that a corticosteroid is absent from the fibrin sealant injected into the disc. This treatment serves to reduce the amount of material from the nucleus fibrosus that leaks through the defect(s) in the annulus fibrosus. The defect can be a tear of the annulus fibrosus, a fissure in the annulus fibrosus, and the like. Advantageously, injection of the fibrin sealant can also serve to restore normal disc height and hydrostatic pressure, a key component. It should be understood that normal physiologic hydrostatic pressure can vary from person to person, and that the treatment may produce near-normal hydrostatic pressure. As used herein, normal physiologic pressure encompasses this range of pressures. In one embodiment, neither the nucleus pulposus nor the annulus fibrosus has been heated in the body to stiffen the disc either prior to or concurrent with the injection, such as discussed in for example U.S. Pat. No. 6,095,149. In one embodiment, in the practice of this invention the nucleus pulposus has not been removed by surgery, such as in the case of a total or partial discectomy or by nucleoplasty for a herniated disc.

In another broad respect, this invention is a method of treating a human back, comprising injecting a fibrin sealant into a disc to seal at least one defect of an annulus fibrosus, wherein the fibrin sealant comprises fibrinogen and an activating compound such as thrombin, wherein the fibrinogen and thrombin forms at least a portion of the fibrin after injection, wherein the fibrinogen, the thrombin, or both has been reconstituted with a solution containing at least one additive, and wherein the fibrin sealant does not include a corticosteroid.

In another broad respect, this invention is a method of treating a human back, comprising providing a mixture of fibrinogen and thrombin within a human disc to treat at least one defect of an annulus fibrosus, wherein the fibrinogen, the thrombin, or both has been reconstituted with a solution containing at least one additive, and wherein a corticosteroid is absent from the mixture. The mixture may be provided into the disc by injection or otherwise.

This invention also includes a kit including components used to inject the fibrin sealant. The kit may comprise fibrinogen, such as freeze-dried fibrinogen, thrombin such as freeze-dried thrombin, at least one additive, and a needle for injecting the sealant such as a spinal needle including for example a curved spinal needle. A spinal canula may alternatively be used. The kit excludes corticosteroid. The kit may exclude a device to provide thermal energy to a disc. The kit can optionally include contrast agent and additional additives. A single, dual or multi-barrel syringe, or other fibrin sealant delivery device, may be included in the kit. The fibrin sealant can be delivered using a convention single lumen needle, or through a bitumen or multilumen needle. If a bitumen needle is used, each component can be delivered through a separate lumen. In one embodiment, a bitumen needle or multilumen needle can be used that allows contact of the fibrinogen component and the thrombin component at the tip of the needle. Alternatively, sequential addition of the fibrinogen component followed by injection of the thrombin or other enzyme component can be used, and these injections can occur in the same needle, multiple needles, or in a bilumen or multilumen needle.

In another broad respect, this invention is a process for manufacturing a kit, comprising: providing a fibrinogen component, a thrombin component, at least one additive, and a spinal needle or a polymeric catheter or both, wherein the kit excludes corticosteroid and wherein the kit excludes a device to provide thermal energy to a disc.

Advantageously, the method and kit of this invention facilitate extended pain relief for patients with leaky disc syndrome, wherein for example nucleus pulposus leaks out of the disc through defects (e.g. tears or fissures) in the annulus fibrosus. Surprisingly, it has been found that the use of fibrin without corticosteroid provides unexpectedly superior results to injections of fibrin sealant that includes a corticosteroid. The present invention provides unexpectedly superior results to the method set forth in U.S. Pat. No. 6,468,527, which discloses the injection of fibrin sealant containing a corticosteroid.

DETAILED DESCRIPTION OF THE INVENTION

Figure 1:
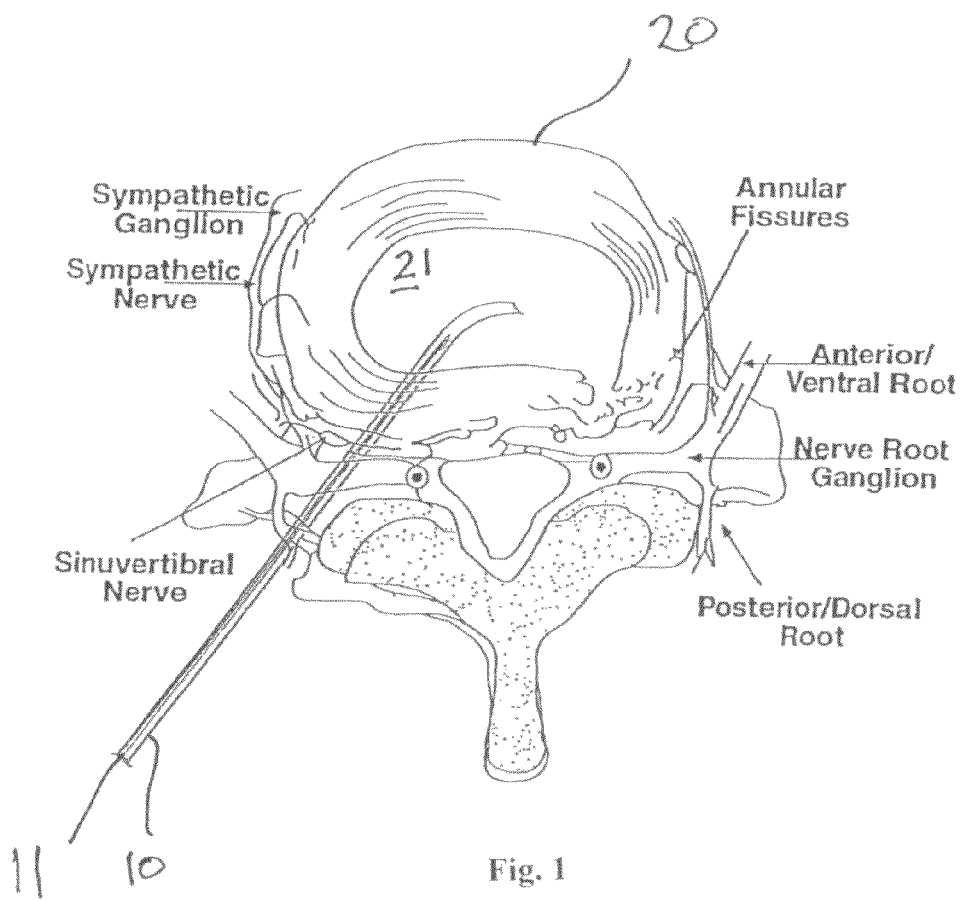
FIG. 1 is a cross-sectional view of a vertebral body at the disk space exhibiting annular fissures which may be treated according to one embodiment of the present invention wherein an introducer needle 10 has been inserted through the annulus fibrosus 21 into the nucleus pulposus 21, and wherein an inner needle or catheter 11 has been inserted into the introducer needle 10 but which does not extend beyond the tip of the introducer needle.
Figure 2:
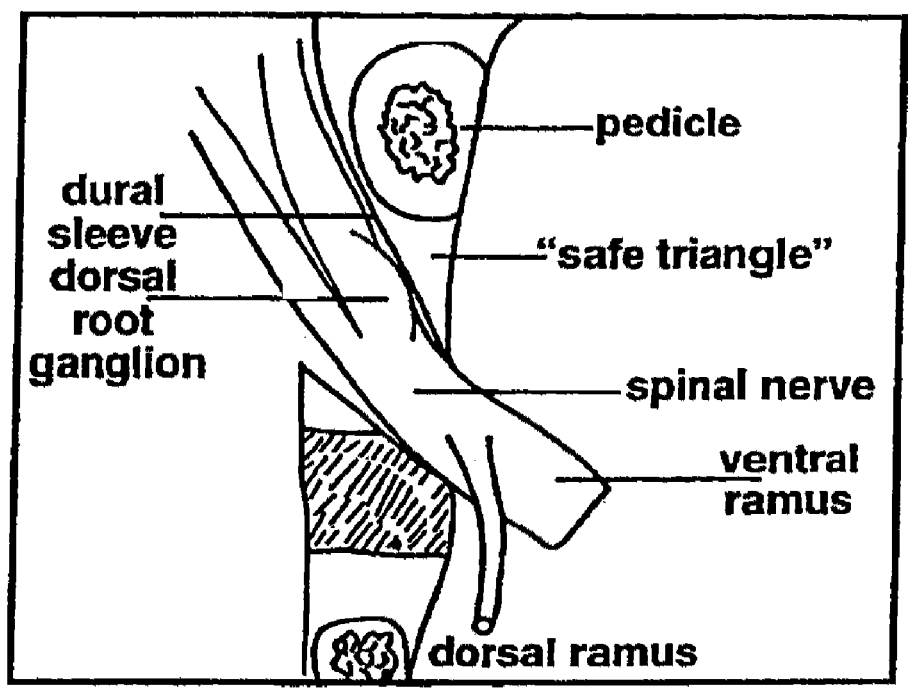
FIG. 2 is a schematic representation of the trans-foraminal space into which the improved sealant may be injected according to one embodiment of the present invention.

The fibrin sealant of the present invention comprises a fibrinogen component and an activating compounds such as thrombin that converts fibrinogen to fibrin. The sealant contains one or more other additives. The fibrinogen, the thrombin, or both is reconstituted with a solution containing at least one of the additives, wherein the additive is other than a corticosteroid. The fibrin sealant is injected into, for example, the disc to seal fissures and tears in the annulus fibrosus. Defects in the annulus fibrosus are commonly diagnosed, currently, using MRI scans and discograms. This can treat both discogenic low back pain and radiculopathy leg pain when injected into the lumbar intervertebral disc.

The fibrinogen used in the practice of this invention includes any fibrinogen that will form fibrin in a human body. Fibrinogen is frequently available in freeze-dried form, and must be reconstituted prior to use. If the thrombin is reconstituted using a solution with an additive, the fibrinogen can also be frozen or fresh, autologous (from the patient to be treated), human including pooled human fibrinogen, recombinant, and bovine or other non-human source such as fish (e.g., salmon and sea trout). The fibrinogen is used in an amount suitable for the given treatment, patient, and so on. Freeze-dried fibrinogen is reconstituted using a solution, typically containing aprotinin and calcium chloride. As discussed herein, either the fibrinogen or thrombin or both is reconstituted with a solution that includes at least one additive. For example, the freeze-dried fibrinogen can be reconstituted using, for example, saline with the additive, a saline solution containing aprotinin and the additive, a saline solution containing the additive and calcium ions ($Ca^{+2}$) such as may be supplied from calcium chloride, or a solution containing combinations of additives.

Thrombin is typically the enzyme used which serves to change fibrinogen to fibrin. However, other enzymes can be used such as those derived from snake venom (e.g., batroxobin), or spider venom as is known in the art. As used herein, "activating compound" refers to a compound that causes fibrinogen to form fibrin, and this term includes thrombin, batroxobin, and so on. Thrombin is available commercially, typically in its freeze-dried form. Freeze-dried thrombin must be reconstituted prior to use. The thrombin can also be frozen or fresh. Thrombin can be autologous, from a human or pooled human supply, bovine, fish (such as salmon) or other non-human fibrinogen-cleaving enzyme source such as various arachnids and other venomous species. The thrombin or enzyme is used in any amount which facilitates changing the fibrinogen to fibrin, as is known to one of skill in the art. The thrombin can be reconstituted using saline and the one or more additives or a saline solution containing the additive and calcium ions.

As used herein, the term "additives" means antibiotics; antiproliferative, cytotoxic, and antitumor drugs including chemotherapeutic drugs; analgesic; antiangiogen; antibody; antivirals; cytokines; colony stimulating factors; proteins; chemoattractants; EDTA; histamine; antihistamine; erythropoietin; antifungals; antiparasitic agents; non-corticosteroid anti-inflammatory agents; anticoagulants; anesthetics including local anesthetics such as lidocaine and bupivicaine; analgesics; oncology agents; cardiovascular drugs; vitamins and other nutritional supplements; hormones; glycoproteins; fibronectin; peptides including polypeptides and proteins; interferons; cartilage inducing factors; protease inhibitors; vasoconstrictors, vasodilators, demineralized bone or bone morphogenic proteins; hormones; lipids; carbohydrates; proteoglycans such as aggrecan (chondrotin sulfate and deratin sulfate), versican, decorin, and biglycan; antiangiogenins; antigens; DBM; hyaluronic acid and salts and derivatives thereof; polysaccharides; cellulose compounds such as methyl cellulose, carboxymethyl cellulose, and hydroxy-propylmethyl cellulose and derivatives thereof; antibodies; gene therapy reagents; genetically altered cells, stem cells including mesenchymal stem cells with transforming growth factor, and/or other cells; cell growth factors to promote rehabilitation of damaged tissue and/or growth of new, healthy tissue such as BMP7 and BMP2; type I and II collagen; elastin; sulfated glycosaminoglycan (sGAG), glucosamine sulfate; pH modifiers; methylsulfonylmethane (MSM); osteogenic compounds; osteoconductive compounds; plasminogen; nucleotides; oligonucleotides; polynucleotides; polymers; osteogenic protein 1 (OP-1 including recombinant OP-1); LMP-1 (Lim Mineralization Protein-1); cartilage including autologous cartilage; oxygen-containing components; enzymes such as, for example, peroxidase, which mediate the release of oxygen from such components; melatonin; vitamins; and nutrients such as, for example, glucose or other sugars. However, it is foreseeable that any of these additives may be added to the fibrin sealant separately or in combination. One or more of these additives can be injected with the fibrinogen and thrombin, or alternatively one or more of these components can be injected separately, either before or after the fibrin sealant has been injected. Combinations of these additives can be employed and different additives can be used in the solutions used to reconstitute the fibrinogen and thrombin (e.g., a solution containing a local anesthetic is used to reconstitute the fibrinogen and a solution containing type II collagen is used to reconstitute the thrombin). In addition, one or more other additives can be added to reconstituted solutions of either thrombin or fibrinogen. Likewise, one or more of these additives can be injected with the fibrinogen and activating compound, or alternatively one or more of these additives can be injected separately, either before or after the fibrin sealant has been injected.

For solutions containing an incompletely water-soluble additive(s), an anti-caking agent such as, for example, polysorbate, may be added to facilitate suspension of this component. Glycol may be inappropriate for use as an anti-caking agent in the instant invention.

It should be appreciated that fibrin formation begins immediately on contact of the fibrinogen and thrombin, such as in the Y-connector of a dual syringe. The term "injecting" of fibrin sealant as used herein thus encompasses any injection of components that form fibrin in the disc, including circumstances where a portion of the components react to form fibrin due to mixing prior to contact with or actual introduction into the disc. It is also within the scope of this invention to sequentially inject the components of the fibrin sealant into the disc, such as by injecting the thrombin component followed by the fibrinogen component, or by injecting the fibrinogen component followed by the thrombin component. Likewise, the fibrinogen component and the thrombin components can be each intermittently injected into the disc.

It should also be appreciated that the point, or points, of injection (e.g., at the tip of a spinal needle) can be within the annulus fibrosus or in the nucleus pulposus. If the injection occurs in the nucleus pulposus, the injected components may form a patch at the interface between the nucleus pulposus and the annulus fibrosus, or, more commonly, the components flow into the defect(s) (e.g., fissures) of the annulus fibrosus and potentially "overflowing" into the interdiscal space. In practice, over-pressurizing the disc by injecting the components into the disc should be avoided.

The fibrinogen and activating compound are injected in amounts effective to seal a given defect of the disc, as is apparent to one of skill in the art. The amount of activating compound such as thrombin can be varied to reduce or lengthen the time to complete fibrin formation. In general, the higher level of thrombin per unit amount of fibrinogen, the faster fibrin formation occurs. If slower fibrin formation is desired, then less thrombin is used per unit fibrinogen. The use of calcium ions (such as from calcium chloride) in one or both of the component solutions will affect the strength of the fibrin so formed, with increasing amount of calcium ions increasing the strength of the fibrin clot. Generally, for a composition comprising fibrinogen that is an aqueous solution, it is believed that from about 3 mL to about 5 mL of such composition is sufficient to be an effective fibrin sealant. However, depending on the use of the composition, the dosage can range from about 0.05 mL to about 40 mL.

Fibrin sealants mimic the final stage of the natural clotting mechanism. Typically, such sealants entail the mixing of a fibrinogen component with an activating enzyme such as thrombin. Thrombin is an enzyme that exists in blood plasma which causes the clotting of blood by converting fibrinogen into fibrin. In normal practice, the components of the fibrin sealant are reconstituted separately, from a freeze-dried state, prior to use. However, use of samples prepared from a frozen state or a fresh state is also acceptable. To increase biocompatibility of the sealant with host tissue, various components may be supplied endogenously from host body fluids. Combining the reconstituted components produces a viscous solution that quickly sets into an elastic coagulum. A method of preparing a conventional fibrin sealant is described by J. Rousou, et al. in Journal of Thoracic and Cardiovascular Surgery, vol. 97, no. 2, pp 194-203, February 1989. Cryoprecipitate derived from source plasma is washed, dissolved in buffer solution, filtered and freeze-dried. The freeze-dried fibrinogen is reconstituted in a fibrinolysis inhibitor solution containing, for example 3000 KIU/ml of aprotinin (a polyvalent protease inhibitor which prevents premature degradation of the formed fibrin), and an additive. The solution is stirred and heated to a temperature of about 37° C. Each solution (the thrombin and fibrinogen solutions) is drawn up in a syringe and mounted on a Y-connector to which a needle is attached for delivery of the combined solution. (See, e.g. the Duploject® device, from ImmunoAG, Vienna, Austria). Thus, mixing of the components only occurs during the delivery process which facilitates clot formation at the desired site of application only. The components should be injected sufficiently quickly to avoid the passage becoming blocked due to fibrin formation in the needle and/or Y-connector.

In one embodiment, the mixing of the fibrin sealant components at least partially occurs in the Y-connector and in the needle mounted on a Y-connector, with the balance of the clotting occurring in the disc. This method of preparation facilitates the formation of a fibrin clot at the desired site in the disc during delivery, or immediately thereafter. Calcium chloride may be included in the fibrin sealant to be injected to modify the composition of the so-formed fibrin and resulting strength of the clot.

In one embodiment, about 75-105 mg/mL of freeze-dried fibrinogen is reconstituted according to conventional methods, and about 45-55 mg/mL thrombin component is reconstituted separately from a freeze-dried state according to the methods and compositions of the present invention. Freeze-dried fibrinogen and freeze-dried thrombin are available in kit-form from such manufacturers as Baxter under names such as TISEEL®. These two fibrin sealant components can be prepared for example in about 2 mL samples each to yield approximately 4 mL of total sealant (reconstituted fibrinogen plus reconstituted thrombin). At least one of the reconstituted fibrinogen and thrombin is reconstituted using a solution containing at least one additive.

While several methods and compositions may be used for preparing the freeze-dried thrombin for use in the invented fibrin sealant, one method is providing about 45-55 mg/mL of freeze-dried thrombin and mixing it with a reconstituting solution. The reconstituting solution for use in reconstituting either the thrombin or fibrinogen, or for both components, may further comprise about 0.1-100 milligrams of another additive described herein (e.g., local anesthetic) and/or calcium chloride. The calcium chloride concentration can be, for example, 1-100 millimoles/mL, and in one embodiment 4-40 millimoles/mL. If employed, the calcium chloride concentration should be sufficient to further the polymerization reaction that forms a durable fibrin sealant clot. A preservative-free reconstituting solution may be desirable, but is not required.

A contrast agent may be used in conjunction with the injection of the fibrin sealant. The contrast agent may be injected prior to injection of the fibrin sealant. Alternatively, the contrast agent is included in the fibrinogen component or thrombin component that is injected into the disc. Contrast agents and their use are well known to one of skill in the art.

Alternative amounts and concentrations of fibrinogen and thrombin may be used to form the desired fibrin sealant clot in the body. For example, as discussed above, varying the fibrinogen and/or thrombin amount/concentration may be done to vary the viscosity and the "setting time" of the combined fibrinogen and thrombin components. Likewise, varying fibrinogen may change the density of the combined components, which may be important for controlling flow through a long conduit such as a catheter into the body. Varying thrombin may vary the polymerization time of the components, which may be important for controlling the time at which the clot forms for ensuring the components set-up at the proper site and time in the body rather than setting-up prematurely.

When acquired in freeze-dried form, the thrombin and fibrinogen need to be reconstituted for use. The thrombin reconstituting solution (e.g., a saline based solution), optionally containing one or more additives, can be prepared in a single vial prior to mixing with the freeze-dried thrombin. This component of the fibrin sealant may then be provided to users in a reconstituted state, or in two uncombined vials containing freeze-dried thrombin and a premixed reconstitution solution. Mixing of the contents of the two vials may be performed at any point up to, and including, the time at which the fibrin sealant (or its components) is injected into the patient. Reconstitution of the fibrinogen solution can be accomplished according to conventional methods. For example, the fibrinogen component may be reconstituted in an aprotinin saline solution which optionally contains additives such as, for example, a local anesthetic. If desired, the thrombin or the fibrinogen or both can be reconstituted using a saline solution that contains one or more additives. All solutions are brought to a temperature of about 37° C. Preferably, the thrombin is combined with the fibrinogen solution using the dual-syringe injection procedure described herein to form a single sealant composition which is injected into a patient. The instant invention provides a vehicle for the delivery of the sealant that conveys the sealant to the precise area of the back, seals any annular fissures, and holds the fibrin in place via the elastic coagulum. In addition, the biodegradable nature of the formed fibrin clot minimizes or eliminates the need for invasive surgical removal following the effective period of use. Therefore, an advantage of the sealant and method of application is the ability to provide a minimally invasive means of accomplishing localized, prolonged sealing of defects (e.g., fissures) in the annulus fibrosus, and if an additive is in the sealant, time-released additive delivery.

The fibrin sealant may be injected into the disc or other body area using procedures well known to one skilled in the art. Typically, an introducer needle is inserted into the intra-discal space with the tip being positioned close to the defect in the annulus fibrosus. A finer gauge needle (made of, e.g., stainless steel and capable of puncturing the annulus fibrosus) is then inserted into the introducer needle. The fibrin sealant is injected through the finer gauge needle. Alternatively, a catheter made from a synthetic polymer can be used. With either a finer gauge needle or a catheter made of synthetic polymer, the needle or catheter can be advanced through the introducer needle and into the nucleus pulposus. Alternatively, the needle or catheter can be advanced up to the tip of the introducer needle, but not far as to go beyond the tip of the introducer needle. This can have the advantage of precisely positioning the point of injection, particularly since a polymeric catheter could bend in the nucleus propulsus thereby become mis-positioned. Likewise by positioning the introducer needle at the desired point of injection as an initial matter, the fibrin sealant can be injected quickly to expedite the procedure, which is a benefit to the patient. In general, the fibrin sealant of this invention is injected into the disc, the epidural space, the zygaphysical (2-joint) joint, the vertebral canal, and/or thecal sac. With respect to an injection of fibrin sealant into a disc, an intra-discal injection serves to create a fibrin matrix which seals the disc from leaking material from the nucleus into the area outside the disc. For example, the fibrin sealant can be delivered by fluoroscopic transforaminal lumber epidural or intra-discal injection, such as described in U.S. Pat. No. 6,468,527. For the treatment of back injuries such as these, the fibrin sealant is injected into the nucleus pulposus, shown in FIG. 1, to fill any fissures or voids of the annulus fibrosus, to seal the bone end plates to the disc, increase pressure of the disc, and to increase the height of the disc space. In general, the fibrin sealant is injected at a location near the defect in the annulus fibrosus. Typically the fibrin sealant will flow into the fissures in the annulus fibrosus, and some fibrin sealant may thus flow out of the intra-discal space. The injection may also serve to coat areas adjacent to the disc, directly on the nerve roots and surrounding areas which serve to protect those areas from the effects of the leaking nucleus material. Sealing the fissures and bone end plates halts the leakage of harmful chemicals into the disc environment and prevents the initiation of foreign-body reactions towards the damaged disc by the immune system. Increasing the disc space relieves pressure on the nerve root. That is, as a result of the injection, an increase of the disc height occurs, which increases the spacing between lamina, and which in turn relieves pressure on the nerve roots on the lamina. For this application, supplementation of the fibrin sealant with growth factors may promote rehabilitation of the damaged tissues or the gradual replacement of the fibrin sealant with healthy tissue.

Use of the improved fibrin sealant composition may be better understood by reference to the following examples. These examples are representative and should not be construed to limit the scope of this invention or claims hereof. Unless otherwise indicated (example 3), corticosteroid is absent from the fibrin sealant being used in these examples and the procedures were conducted in the absence of a heating step of the nucleus fibrosus and annulus fibrosus and in the absence of a partial or total discectomy.

EXAMPLE 1

Fluoroscopic Transforaminal Epidural Injection

With a patient in the prone position on the imaging table, a fluoroscope is positioned and adjusted to locate the intervertebral foramen of the affected nerve root. A curved 22 ga.×3.5" needle is introduced after anesthetizing the skin and deep tissue. The needle is advanced under direct fluoroscopic vision to a position in the anterior epidural space. Positioning of the needle is verified by a lateral fluoroscopic view and by injecting contrast medium through the needle. Such positioning may or may not require further adjustment. If adjusted, location of the needle is once again verified. Advancement of the needle into the correct region may stimulate pain in a manner consistent with the initial complaint. Therefore, needle placement may also be verified by the patient's pain recognition. The epidural space is anesthetized with injectable anesthetic. The fibrin sealant of fibrinogen and thrombin (prior to clotting) is then introduced through the needle with continuous gentle pressure until the volumes of the dual syringe system are sufficiently depleted. The thrombin or fibrinogen or both has been reconstituted with a solution containing at least one additive. The fibrin sealant then coats the nerve root and annulus and the needle is withdrawn. Patient observation and vital signs monitoring is performed for about 20-30 minutes following the procedure.

For this procedure, a sufficient volume of the fibrin sealant is injected to effectively hydro-dissect the area around the targeted nerve root. It is believed that due to the avascular nature of the epidural space, the absorption/degradation period is typically longer than that observed for open applications in regions with greater vascularity and exposure to room air at the time of application.

The ability of the fibrin sealant to seal annular fissures related to disc herniation offers a therapeutic benefit to patients. Chemical radiculitis, or inflammation of the nerve root, is known to be quite painful in some instances. It is believed that use of the fibrin sealant in the above described manner not only coats the nerve root, but also seals annular fissures surrounding the herniated disk. (See FIG. 1). As a result of the hydro-dissection of the area around the affected nerve root, the sealant also seals annular fissures from outside the annulus.

EXAMPLE 2

Fluoroscopic Guided Intra-Discal Injection

After sterile preparation, an introducer needle is advanced in oblique projection to a superior articular process. A curved spinal needle is advanced through the introducer needle into the disc. Both anterior-posterior and lateral fluoroscopic projections are used to confirm proper needle placement. If the needle placement needs to be adjusted, placement is again confirmed fluoroscopically. A contrast agent is injected to confirm needle placement. In patients with chemical radiculitis, the contrast agent can be observed to be leaking through the annular fissures and/or intra-discal pathology can be identified. Once the needle is properly positioned in the intra-discal space, the fibrin sealant (or its components) is injected. The thrombin or fibrinogen or both has been reconstituted with a solution containing at least one additive. The fibrin sealant is observed to force the contrast agent from the intra-discal space as it seals the annual fissures. Alternatively, the contrast agent is injected with the sealant. Alternatively, no contrast agent is used. The procedure seals the defects/fissures of the annulus fibrosus and stops the chemical leakage and facilitates regeneration within the disc.

EXAMPLE 3

Figure 3:
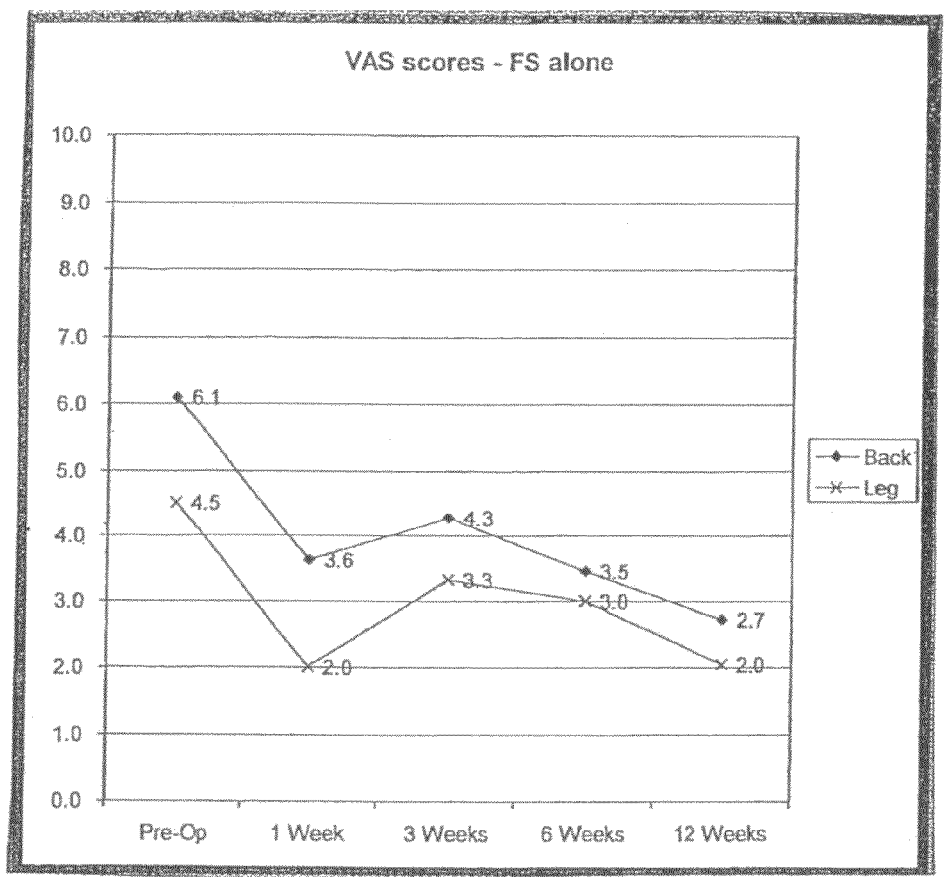
FIGS. 3 and 4 show graphs of the VAS scores from example 3.
Figure 4:
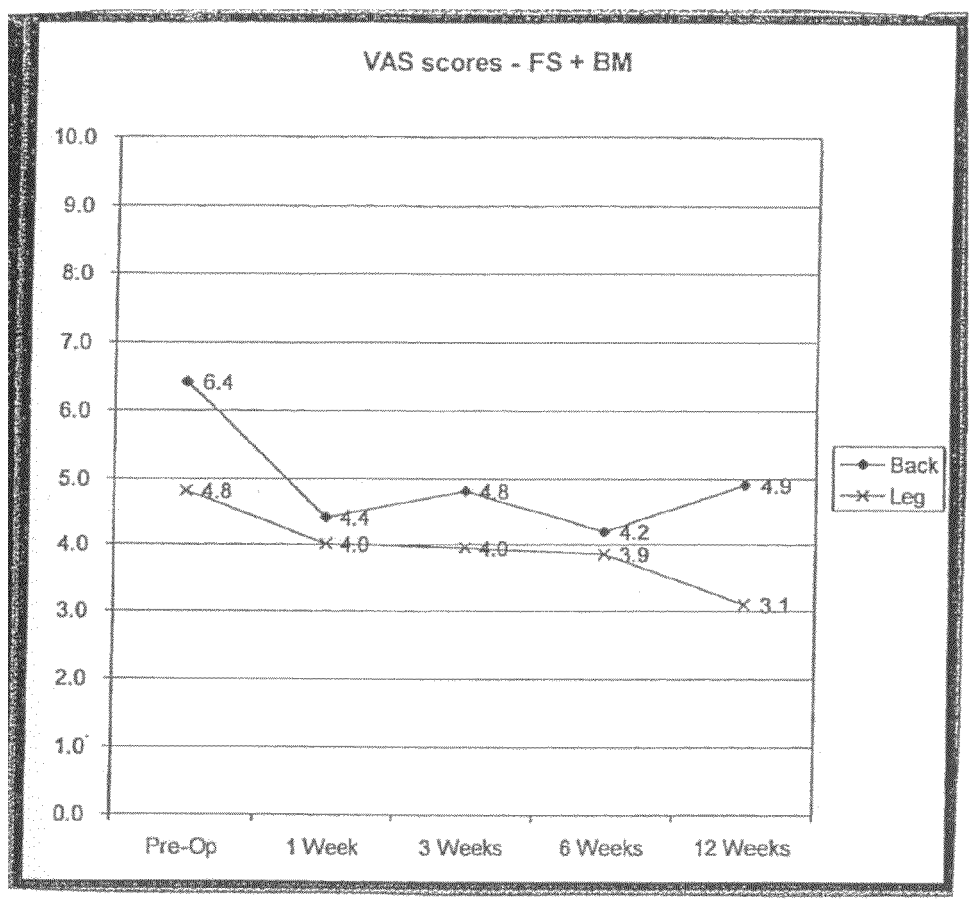

Comparison of Injection of Fibrin Sealant Injection of Fibrin Sealant Containing a Corticosteriod Twenty patients were split into two 10-patient groups. All of the patients suffered from pain due to disc degeneration caused by defects (fissures) in the annulus fibrosus. All of the patients had previously failed at least 6 months of traditional conservative therapy. Using the procedure in example 2, the first group of patients was intra-discally injected with fibrin sealant containing fibrinogen and thrombin. Using the procedure in example 2, the second group of patients was intra-discally injected with fibrin sealant containing fibrinogen, thrombin, and betamethasone (a corticosteroid). The corticosteroid was in the thrombin component. Each patient rated back and leg pain on a scale of 0 to 10, before and at pre-defined intervals following surgery. The results (VAS scores) are shown in FIGS. 3 and 4. As can be seen, the patients that were injected with fibrin sealant alone (without betamethasone) experienced superior pain relief to those patients that were injected with fibrin sealant containing betamethasone. It had been anticipated that the patients receiving injections that included betamethasone would experience superior results due to the action of the betamethasone to reduce inflammation. However, the opposite was observed. Indeed, the patients injected with fibrin sealant only experienced significantly improved pain relief, not only after one week from surgery, but especially 12 weeks after surgery. These results were surprising and unexpected.

EXAMPLE 4

Fibrin Sealant Reconstituted with a Local Anesthetic

A patient was treated with fibrin sealant containing a local anesthetic. The local anesthetic was used to reconstitute the thrombin. The patient suffered from pain due to disc degeneration caused by defects (fissures) in the annulus fibrosus. Using the procedure in example 2, the patient was intra-discally injected with fibrin sealant containing fibrinogen, thrombin, and a local anesthetic (3 cc of 0.75% bupivacaine). Local anesthetic was used reconstitute the thrombin. A total of 5 cc of fibrinogen, thrombin, and local anesthetic was injected. The patient rated back and leg pain on a scale of 0 to 10, before and at predefined intervals following surgery. The results were as follows for back pain: pre-treatment, 4; 1 week after treatment, 4, 3 weeks after treatment, 1; and after 6 weeks, 1. Leg pain was zero both at pre-treatment and after treatment. Owing to the dramatic decrease in pain after 6 weeks, these results were surprising and unexpected.

It is envisioned that the present invention may be used to address various conditions through use of the fibrin sealant in a manner similar to that described in the examples above. Discussion of this invention referenced particular means, materials and embodiments elaborating limited application of the claimed invention. The invention is not limited to these particulars and applies to all equivalents. Although this invention has been described above with reference to particular means, materials and embodiments, it is to be understood that the invention is not limited to these disclosed particulars, but extends instead to all equivalents within the scope of the following claims.

What is claimed is:

1. A method of treating a disc that is leaking nucleus pulposus through at least one defect in the annulus fibrosus, comprising: injecting a fibrin sealant into the disc to reduce at least a portion of the at least one defect, wherein the fibrin sealant injected into the disc comprises fibrinogen and thrombin, wherein at least a portion of the fibrin forms after injection, wherein the fibrinogen, the thrombin or both has been reconstituted with a solution containing at least one additive, wherein a corticosteroid is absent from the fibrin sealant injected into the disc, and wherein the injecting occurs by inserting an introducer needle having a tip into the intra-discal space to a position adjacent to the at least one defect, inserting a second needle or a polymeric catheter through the introducer needle up to but not beyond the tip of the introducer needle, and injecting the fibrin sealant through the second needle or polymeric catheter.

2. The method of claim 1, wherein neither the nucleus pulposus nor the annulus fibrosus has been heated.

3. The method of claim 1, wherein the fibrin sealant consists essentially of fibrinogen, thrombin and the at least one additive, and optionally calcium chloride.

4. The method of claim 1, wherein the fibrin sealant consists of fibrinogen, thrombin, and the at least one additive, and optionally containing calcium chloride.

5. The method of claim 1, wherein the fibrin sealant further comprises calcium chloride which is injected with the fibrinogen and the activating compound.

6. The method of claim 1, wherein the method consists of the injecting step.

7. The method of claim 1, wherein the additive is selected from the group consisting of antibiotics; antiproliferative, cytotoxic, and antitumor drugs including chemotherapeutic drugs; analgesic; antiangiogen; antibody; antivirals; cytokines; colony stimulating factors; proteins; chemoattractants; EDTA; histamine; antihistamine; erythropoietin; antifungals; antiparasitic agents; non-corticosteroid anti-inflammatory agents; anticoagulants; anesthetics; analgesics; oncology agents; cardiovascular drugs; glycoproteins; fibronectin; peptides including polypeptides and proteins; interferons; cartilage inducing factors; protease inhibitors; vasoconstrictors, vasodilators, demineralized bone or bone morphogenetic proteins; hormones; lipids; carbohydrates; proteoglycans; antiangiogenins; antigens; DBM; hyaluronic acid and salts and derivatives thereof; polysaccharides; cellulose compounds and derivatives thereof; gene therapy reagents; genetically altered cells, stem cells including mesenchymal stem cells with transforming growth factor, and/or other cells; cell growth factors; type II collagen; elastin; sulfated glycosaminoglycan (sGAG), glucosamine sulfate; pH modifiers; methylsulfonylmethane (MSM); osteogenic compounds; osteoconductive compounds; plasminogen; nucleotides; oligonucleotides; polynucleotides; polymers; osteogenic protein 1 (oP-1 including recombinant OP-1); LMP-1 (Lim Mineralization Protein-1); cartilage; oxygen-containing components; enzymes; melatonin; vitamins; and nutrients.

8. The method of claim 1, wherein at least one additive is a local anesthetic.

9. The method of claim 1, wherein no portion of the nucleus pulposus has been removed by surgery.

10. The method of claim 1, wherein the at least one defect is a tear or fissure in the annulus fibrosus.

11. The method of claim 1, wherein normal hydrostatic pressure in the disc is restored or normal disc height is restored or both.

12. The method of claim 1, wherein the fibrinogen is autologous.

13. The method of claim 1, wherein the injection is performed using a dual barrel syringe.

14. The method of claim 1, wherein a mixture of fibrinogen and thrombin is injected.

15. The method of claim 1, wherein the fibrinogen and thrombin are injected sequentially and at least partially mix in the disc.

16. The method of claim 1, wherein the additives are injected sequentially either before with or after the fibrinogen and thrombin and at least partially mix in the disc.

17. The method of claim 1, wherein the disc is injected with the fibrin sealant at multiple points.

18. The method of claim 1, wherein the disc is a lumbar disc.

19. The method of claim 1, wherein the disc is a cervical disc.

20. The method of claim 1, wherein the disc is a thoracic disc.

21. The method of claim 1, wherein a contrast agent is injected either before the fibrin sealant, with the fibrin sealant, or after the fibrin sealant has been injected.

22. A kit, comprising: fibrinogen, thrombin, at least one additive, a first needle having a tip, a spinal needle having a tip or a polymeric catheter having a tip or both a spinal needle and a polymeric catheter, wherein the length of the spinal needle and polymeric catheter is configured such that the tip of the spinal needle and the tip of the polymeric catheter do not extend past the tip of the first needle during use, wherein the kit excludes corticosteroid and wherein the kit excludes a device to provide thermal energy to a disc.

23. A process for manufacturing a kit, comprising: providing a fibrinogen component, a thrombin component, at least one additive, a first needle having a tip, and a spinal needle having a tip or a polymeric catheter having a tip or both a spinal needle and a polymeric catheter, wherein the length of the spinal needle and polymeric catheter is configured such that the tip of the spinal needle and the tip of the polymeric catheter do not extend past the tip of the first needle during use, wherein the kit excludes corticosteroid and wherein the kit excludes a device to provide thermal energy to a disc.

24. A method of treating a disc having an intra-discal space, comprising:
   percutaneously inserting an introducer needle having a tip into the intra-discal space,
   inserting a second needle through the introducer needle up to but not beyond the tip of the introducer needle, and
   injecting a fibrin sealant into the disc, wherein the fibrin sealant comprises fibrinogen, thrombin, and an additive,
   wherein at least a portion of the fibrin forms after injection, and
   wherein a corticosteroid is absent from the fibrin sealant injected into the disc.

25. The method of claim 24, wherein the injecting occurs by injecting the fibrin sealant through the second needle or polymeric catheter.

26. The method of claim 1, wherein the only thrombin injected is the reconstituted thrombin.

* * * * *